United States Patent [19]

Rekers

[11] Patent Number: 4,515,666
[45] Date of Patent: May 7, 1985

[54] RADIATION-STABLE POLYOLEFIN COMPOSITIONS CONTAINING AROMATIC KETONE COMPOUNDS

[75] Inventor: John W. Rekers, Spartanburg, S.C.

[73] Assignee: Milliken Research Corporation, Spartanburg, S.C.

[21] Appl. No.: 470,189

[22] Filed: Feb. 28, 1983

[51] Int. Cl.³ .......................... C08K 5/13; C08K 5/07
[52] U.S. Cl. .......................... 204/159.2; 524/347; 524/359
[58] Field of Search ............... 524/347, 359; 523/124, 523/125; 204/159.2, 159.22, 159.23; 252/404, 407; 568/304, 332

[56] References Cited

U.S. PATENT DOCUMENTS

| | | | |
|---|---|---|---|
| 3,537,967 | 11/1970 | Kelly et al. | 204/159.2 |
| 3,846,395 | 11/1974 | Harper et al. | 523/125 |
| 3,888,804 | 6/1975 | Swanholm et al. | 524/359 |
| 3,940,325 | 3/1976 | Hirao | 204/159.2 |
| 3,992,349 | 11/1976 | Sparks | 523/125 |
| 4,431,497 | 2/1984 | Rekers | 204/159.2 |

Primary Examiner—V. P. Hoke
Attorney, Agent, or Firm—H. William Petry; Terry T. Moyer

[57] ABSTRACT

An olefinic polymer composition is provided which comprises an olefinic polymer selected from homopolymers and copolymers made from aliphatic, ethylenically unsaturated monomers containing from 2 to about 10 carbon atoms; from about 100 to about 3,000 parts per million based on the weight of the total composition of a hindered phenolic stabilizer; and from about 100 to about 10,000 ppm based on the weight of the composition of a stabilizer selected from compounds of the formula:

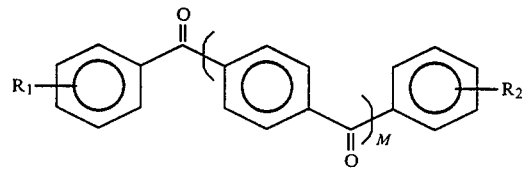

wherein M is 0 or 1; $R_1$ and $R_2$ are each independently selected from hydrogen or an alkyl group containing from 1 to about 20 carbon atoms.

2 Claims, No Drawings

RADIATION-STABLE POLYOLEFIN COMPOSITIONS CONTAINING AROMATIC KETONE COMPOUNDS

The present invention relates to compositions of olefinic polymers suitable for high energy radiation treatment. More particularly, the present invention relates to olefinic polymer compositions which are stable to sterilizing dosages of high energy radiation such as gamma radiation.

Olefinic polymers, such as polyethylene and polypropylene, have a wide variety of known end use applications. Recently, as disclosed for instance in U.S. Pat. No. 3,940,325 to Hirao (Chisso), olefinic polymers have been disclosed to be useful in the manufacture of shaped articles for medical uses and for food packaging uses where the articles must undergo sterilization or be disinfected. It has also been reported that sterilization of such shaped articles may advantageously be accomplished by irradiating the article with high energy radiation such as gamma radiation.

Notwithstanding the significant known advantages of sterilization by means of high energy radiation, several disadvantages are known to be associated with such sterilization techniques. First, when treated with radiation energy in an amount sufficient to achieve the desired sterilization, such polyolefin compositions may become discolored. As reported in U.S. Pat. No. 3,537,967 to Kelly et al. (Dart Industries), this coloration may occur for a variety of reasons such as the use of certain additives in the polymer, as well as the presence of high amounts of catalytic residues such as titanium and chlorine. Simple removal of the additives from the olefinic polymer composition has not been found to be a satisfactory solution to the problem because, as reported by Hirao, while polymers which do not contain the standard additives may not be subject to such coloration, the physical properties of the shaped articles made from such polymers after irradiation with, for instance, γ-rays may be disadvantageously degraded.

Some of the most common additives found in polyolefin polymer compositions to be made into shaped articles, especially where increased melt temperatures of higher melt index polymers are required are the so-called primary antioxidants employed to retard radical chain oxidation. The most common primary antioxidants are phenolic in nature. Examples include Goodrite 3114 and 3125 which are phenolic antioxidants available from B. F. Goodrich Chemical Company. When used at effective concentrations to provide both processing and radiation stability these compounds have been found to cause the shaped article, which has been irradiated with a sterilizing dose, to be unacceptably discolored.

Accordingly, it would be highly desirable to provide olefinic polymer compositions which may be made into shaped articles that may be irradiated with sterilizing amounts of radiation while minimizing or eliminating undesirable discoloration or degradation in physical properties. The olefinic polymer compositions and shaped articles made therefrom according to the present invention may be employed to accomplish such desirable result.

According to the present invention an olefinic polymer composition is provided which comprises an olefinic polymer selected from homopolymers and copolymers made from aliphatic, ethylenically unsaturated monomers containing from 2 to about 10 carbon atoms; from about 100 to about 3,000 parts per million based on the weight of the total composition of a hindered phenolic stabilizer; and from about 100 to about 10,000 ppm based on the weight of the composition of a stabilizer selected from compounds of the formula:

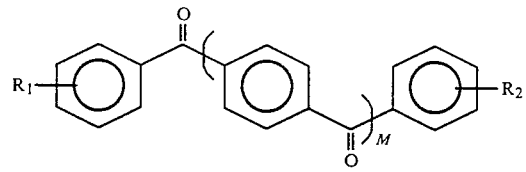

wherein M is 0 or 1; $R_1$ and $R_2$ are each independently selected from hydrogen or an alkyl group containing from 1 to about 20 carbon atoms.

The alkyl groups referred to above may be straight chain, branched chain or even cyclic alkyl groups. Examples of alkyl groups which may be employed include methyl, ethyl, isopropyl, tert-butyl, nonyl, dodecyl and eicosyl groups.

The present invention also relates to an additive package for an olefinic polymer composition which comprises 100 parts of a hindered phenolic stabilizer; and from about 20 to about 2000 parts of a stabilizer selected from compounds of the formula:

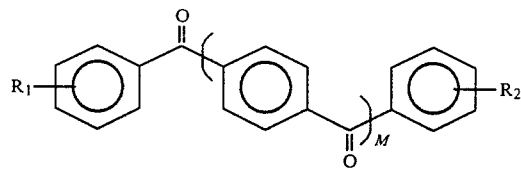

wherein M is 0 or 1; $R_1$ and $R_2$ are each independently selected from hydrogen or an alkyl group containing from 1 to about 20 carbon atoms.

The stabilizers which may be employed according to the present invention may be very broadly described as having the structural formula set forth above. In general such stabilizers may be employed in an amount of from about 100 to about 10,000 parts per million (ppm) based on the weight of the total composition. Preferably, the amount employed may be from about 500 to about 5,000 ppm. Examples of preferred stabilizers that may be employed include aromatic ketone compounds such as those set forth in Table I below:

TABLE I

| Structure | Name |
|---|---|
| (structure) | benzophenone |
| (structure) | 4,4'-di-t-butylbenzophenone |
| (structure) | 1,4-dibenzoylbenzene |

TABLE I-continued

| Structure | Name |
|---|---|
| [structure] | 1,4-di(4'-methylbenzoyl)benzene |
| [structure] | 1,4-di(4'-t-butylbenzoyl)benzene |
| [structure] | 1,4-bis(2',4'-dimethylbenzoyl)-benzene |

It has been found that the olefinic compositions may contain one or more kown, phenolic based, primary stabilizers, such as hindered phenolic-type compounds in addition to the aromatic ketone compound. This discovery is particularly significant since it may not be possible in the practical world to process polypropylene without a phenolic primary antioxidant, the presence of which may lead to yellowing on irradiation. The present invention may provide a remedy for this phenomenon. In such instance, even stabilizers which have been observed to cause discoloration in the polymer composition when subjected to radiation sterilization may not cause such discoloration when the aromatic ketone compound is also present in the composition. Such primary stabilizers may be provided in the composition in an amount of from about 100 to about 3,000 ppm, preferably from about 500 to about 2,000 ppm.

The olefinic polymer compositions of the present invention may also include one or more so-called secondary antioxidants or synergists. These secondary antioxidants are known for use in association with phenolic-type primary stabilizers and include a wide variety of compounds which in general may function by converting harmful peroxide compounds present in the polymeric composition to non-harmful, non-radical product. Examples of such secondary antioxidants include dilauryl thiodipropionate, distearyl thiodipropionate, trisnonylphenyl phosphite, dilauryl phosphite, and Weston 618 and Weston 619, which are phosphorus-containing antioxidants available from Borg Warner. In general, such secondary stabilizers may be used in an amount of from about 100 to about 10,000, preferably about 500 to about 3,000 ppm.

Olefinic polymers that may be employed according to the present invention include a wide range of olefinic homopolymers and copolymers of ethylene, propylene, butylene and higher homologues containing up to about 10 carbon atoms. Typically such polymers may have a molecular weight of from about 10,000 to about 500,000, preferably about 30,000 to about 300,000. The preferred polymers applicable for use according to this invention are homopolymers of propylene and random or block copolymers of propylene with other mono-α-olefins such as ethylene, butene-1 and higher homologues containing up to 10 carbon atoms. Blends of such propylene polymers with other polymers such as polyethylene are also included within the scope of this invention. Generally the proportion of polymerized propylene in the total resin phase of the composition should be at least about 60 percent by weight.

In general, the radiation treatment can be applied to polymers of propylene useful particularly for medical purposes although this particular end use should not be understood to be a limitation upon the scope of the present invention. Thus, for instance, the olefinic polymer compositions of the present invention may be employed for other end uses where such radiation treatment is necessary or desirable, e.g., meat packaging, preserving food in retail packages and other uses.

The high energy radiation treatment of the olefinic polymer compositions of the present invention may include any of a wide variety of know treatment techniques. One convenient radiation source is a cobalt 60 source. Other radiation treatments that may be employed include high energy x-rays, or high energy electrons ($\beta$-radiation). In general, radiation dosages that can be applied may range up to about 5 megarads. For sterilization purposes, a shaped article may be generally sterilized by applying 2.5 megarads under gamma radiation.

The following examples are provided to illustrate the invention but are not to be construed as unduly limiting the subject matter thereof which is defined in the appended claims.

EXAMPLE 1

Preparation of 1,4-dibenzoylbenzene

To a stirred slurry of 50 g of aluminium chloride in 150 ml of benzene under reflux was added dropwise 40 g of terephthaloyl chloride dissolved in 250 ml of benzene. When the addition was complete the reaction was refluxed for 15 minutes, and 250 ml of water was added slowly. The benzene layer was separated and the aqueous layer was extracted with methylene chloride (2×300 ml). The combined orgainic layers were washed with 1m NaOH solution (2×400 ml) and water (400 ml), dried (MgSO$_4$), filtered, and the solvents were removed under reduced pressure to give a nearly colorless solid. Recrystallization from 95% ethanol gave 46.8 g of colorless 1,4-dibenzoylbenzene, m.p. 160°–162°.

EXAMPLE 2

Preparation of 1,4-di(4'-t-butylbenzoyl)benzene

This derivative was prepared as in the example above. From 28 g of aluminium chloride, 275 ml of t-butylbenzene, and 20 g of terephthaloyl chloride there was obtained 11.8 g of the colorless material, m.p. 159°–161°.

EXAMPLE 3

Preparation of 1,4-di(4'-methylbenzoyl)benzene

To a stirred mixture of 40 g of terephthaloyl chloride and 200 ml of toluene was added in portions 56 g of solid aluminium chloride at such a rate to maintain the reaction temperature at 45°–55°. The thick orange slurry was then heated to 75° for 2 hours, cooled in ice and slowly treated with 200 ml of dilute HCL. The slurry was stirred for 2 hours at room temperature. The solid was collected by filtration, washed with 200 ml of petroleum ether and 2 L of hot water, and dried to constant weight to give 51 g of colorless product, m.p. 178°–187°. This material was used without further purification.

EXAMPLE 4

Preparation of 1,4-bis(2', 4'-dimethylbenzoyl)benzene

This derivative was prepared as in the example above. From 40 g of terephthaloyl chloride 150 ml of m-xylene, and 56 g of aluminium chloride in 100 ml of hexane there was obtained 54.3 g of the colorless product, m.p. 128°–132°. This material was used without further purification.

EXAMPLE 5

Preparation of 4,4'-di-tert-butylbenzophenone

To a cold stirred mixture of 45.3 g of aluminium chloride in 100 ml of carbon tetrachloride was added dropwise over 2 hours 89.9 g of tert-butybenzene in 41 ml of carbon tetrachloride. When the addition was complete the mixture was stirred for 3 hours with cooling and allowed to stand 18 hours at room temperature. The reaction was cooled in ice and 50 ml of water was added dropwise. The resulting mixture was slowly heated to 110° with distillation of excess carbon tetrachloride and water. After cooling the reaction was extracted with ether (700 ml). The organic solution was washed with dilute NaOH (200 ml) and brine (200 ml), dried (MgSO$_4$) and solvent removed under reduced pressure. The resulting solid was washed with cold petroleum ether to give 29.4 g of the light tan benzophenone derivative, m.p. 132°–136°.

EXAMPLE 6

The additives were blended into polypropylene powder (Hercules Profax 6301) extruded into pellets, and injection molded into 55 mil thick plaques. The molded samples were irradiated to a 5 mrad dose with a cobalt-60 γ-ray source, and subsequently aged for four weeks at 50° C. in a forced air oven. Yellowness indices were measured on a Hunter Colorimeter (ASTM D 1925) before and after ageing. This data for various additive formulations is shown in Table II.

TABLE II

| Entry | Additives | (% by wt.) | Yellowness Index Unaged | Aged |
|---|---|---|---|---|
| 1 | Goodrite 3114 | (0.1%) | 7.6 | 9.2 |
| 2 | benzophenone | (0.2%) | 1.4 | 1.7 |
| 3 | benzophenone | (0.1%) | 3.8 | 4.2 |
|   | Goodrite 3114 | (0.1%) |   |   |
| 4 | 4,4'-di-t-butyl-benzophenone | (0.2%) | 1.3 | 1.3 |
| 5 | 4,4'-di-t-butyl-benzophenone | (0.1%) | 3.8 | 4.2 |
|   | Goodrite 3114 | (0.1%) |   |   |
| 6 | 1,4-dibenzoyl-benzene | (0.2%) | 1.8 | 3.0 |
| 7 | 1,4-dibenzoyl-benzene | (0.1%) | 4.2 | 4.2 |
|   | Goodrite 3114 | (0.1%) |   |   |
| 8 | 1,4-di(4'-methyl-benzoyl)benzene | (0.2%) | 2.1 | 4.1 |
| 9 | 1,4-di(4'-methyl-benzoyl)benzene | (0.1%) | 4.3 | 4.4 |
|   | Goodrite 3114 | (0.1%) |   |   |
| 10 | 1,4-di(4'-t-butyl-benzoyl)benzene | (0.2%) | 1.5 | 2.5 |
| 11 | 1,4-di(4'-t-butyl-benzoyl)benzene | (0.1%) | 3.8 | 3.9 |
|   | Goodrite 3114 | (0.1%) |   |   |
| 12 | 1,4-bis(2',4'-di-methylbenzoyl)-benzene | (0.2%) | 7.2 | 8.6 |
| 13 | 1,4-bis(2',4'-di-methylbenzoyl)-benzene | (0.1%) | 8.2 | 7.7 |
|   | Goodrite 3114 | (0.1%) |   |   |
| 14 | None |   | 1.9 | 1.6 |

EXAMPLE 7

Injection molded polypropylene tensile bars were prepared, irradiated and aged as in Example 4. As a measure of relative embrittlement, percent elongation at break was recorded before and after ageing on an Instron testing machine (ASTM D 633, 100% strain rate). This data for various additive formulations is shown in Table III.

TABLE III

| Entry | Additives | (% by wt.) | % Elongation at Break Unaged | Aged |
|---|---|---|---|---|
| 1 | Goodrite 3114 | (0.1%) | 30 | 25 |
| 2 | benzophenone | (0.2%) | 90 | 5 |
| 3 | benzophenone | (0.1%) | 800 | 30 |
|   | Goodrite 3114 | (0.1%) |   |   |
| 4 | 4,4'-di-t-butyl-benzophenone | (0.2%) | 30 | 5 |
| 5 | 4,4'-di-t-butyl-benzophenone | (0.1%) | 250 | 25 |
|   | Goodrite 3114 | (0.1%) |   |   |
| 6 | 1,4-dibenzoyl-benzene | (0.2%) | 30 | 5 |
| 7 | 1,4-dibenzoyl-benzene | (0.1%) | 150 | 30 |
|   | Goodrite 3114 | (0.1%) |   |   |
| 8 | 1,4-di(4'-methyl-benzoyl)benzene | (0.2%) | 155 | 5 |
| 9 | 1,4-di(4'-methyl-benzoyl)benzene | (0.1%) | 440 | 25 |
|   | Goodrite 3114 | (0.1%) |   |   |
| 10 | 1,4-di(4'-t-butyl-benzoyl)benzene | (0.2%) | 30 | 5 |
| 11 | 1,4-di(4'-t-butyl-benzoyl)benzene | (0.1%) | 125 | 25 |
|   | Goodrite 3114 | (0.1%) |   |   |
| 12 | 1,4-bis(2',4'-di-methylbenzoyl)-benzene | (0.2%) | 110 | 5 |
| 13 | 1,4-bis(2',4'-di methylbenzoyl)-benzene | (0.1%) | 650 | 25 |
|   | Goodrite 3114 | (0.1%) |   |   |
| 14 | None |   | 70 | 5 |

What is claimed is:

1. A method for sterilizing a shaped article made from an olefinic polymer composition which comprises subjecting said shaped article to high energy radiation in an amount sufficient to sterilize said shaped article; said olefinic polymer composition comprising an olefinic polymer selected from homopolymers and copolymers made from aliphatic, ethylenically unsaturated monomers containing from 2 to about 10 carbon atoms; from about 100 to about 3,000 parts per million based upon the weight of the total composition of a hindered phenolic stabilizer; and from about 100 to about 10,000 parts per million based upon the weight of the composition of a stabilizer selected from compounds of the formula:

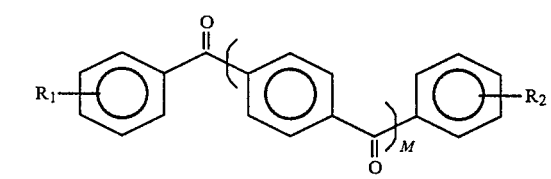

wherein M is 0 or 1; $R_1$ and $R_2$ are each independently selected from hydrogen or an alkyl group containing from 1 to about 20 carbon atoms.

2. A process according to claim 1 wherein said high energy radiation is gamma radiation.

UNITED STATES PATENT AND TRADEMARK OFFICE
CERTIFICATE OF CORRECTION

PATENT NO. : 4,515,666

DATED : May 7, 1985

INVENTOR(S) : John W. Rekers

It is certified that error appears in the above-identified patent and that said Letters Patent is hereby corrected as shown below:

Column 1, line 46, change "of" to --or--.

Column 4, line 35, after "15 minutes," add --cooled--.

Column 4, line 39, change "1m" to --1$\underline{m}$--.

Column 5, line 16, change "tert-butybenzene" to --$\underline{tert}$-butybenzene--.

Signed and Sealed this

Sixteenth Day of September 1986

[SEAL]

Attest:

DONALD J. QUIGG

Attesting Officer

Commissioner of Patents and Trademarks